(12) United States Patent
Madejón Seiz et al.

(10) Patent No.: US 7,919,244 B2
(45) Date of Patent: Apr. 5, 2011

(54) NUCLEIC ACID DETECTION METHOD INVOLVING THE DIRECT GENERATION OF A MEASURABLE SIGNAL

(75) Inventors: Antonio Madejón Seiz, Madrid (ES); Francisco Javier Calvo Macarro, Madrid (ES); Pedro Manuel Franco De Sarabia Rosado, Madrid (ES); Gemma Rocio Limones Lopez, Madrid (ES); Sonia Rodriguez Gil, Madrid (ES)

(73) Assignee: Biotools Biotechnological & Medical Laboratories, S.A., Madrid (ES)

( * ) Notice: Subject to any disclaimer, the term of this patent is extended or adjusted under 35 U.S.C. 154(b) by 131 days.

(21) Appl. No.: 11/666,468

(22) PCT Filed: Jun. 16, 2005

(86) PCT No.: PCT/ES2005/070093
§ 371 (c)(1),
(2), (4) Date: Apr. 27, 2007

(87) PCT Pub. No.: WO2006/136621
PCT Pub. Date: Dec. 28, 2006

(65) Prior Publication Data
US 2007/0292868 A1    Dec. 20, 2007

(51) Int. Cl.
*C12Q 1/68* (2006.01)
*C07H 21/02* (2006.01)
*C07H 21/04* (2006.01)

(52) U.S. Cl. .................... 435/6; 536/23.1; 536/24.3

(58) Field of Classification Search ..... 435/6; 536/23.1, 536/24.3
See application file for complete search history.

(56) References Cited

U.S. PATENT DOCUMENTS

| | | | |
|---|---|---|---|
| 5,639,611 A * | 6/1997 | Wallace et al. ............... | 435/6 |
| 5,874,283 A * | 2/1999 | Harrington et al. ........ | 435/252.3 |
| 5,925,517 A * | 7/1999 | Tyagi et al. ................ | 435/6 |
| 6,248,526 B1 * | 6/2001 | Weimer ..................... | 435/6 |
| 6,350,580 B1 * | 2/2002 | Sorge ......................... | 435/6 |
| 6,528,254 B1 * | 3/2003 | Sorge ......................... | 435/6 |
| 2002/0061532 A1 * | 5/2002 | Adams et al. ............... | 435/6 |
| 2003/0003468 A1 * | 1/2003 | Crow .......................... | 435/6 |
| 2003/0143591 A1 | 7/2003 | Davies et al. | |
| 2004/0053287 A1 * | 3/2004 | Lawler, Jr. ................. | 435/6 |
| 2004/0072247 A1 * | 4/2004 | Pfistershammer ......... | 435/7.1 |
| 2005/0026166 A1 * | 2/2005 | Bi ............................... | 435/6 |
| 2006/0073508 A1 * | 4/2006 | Small et al. ................ | 435/6 |
| 2007/0134686 A1 * | 6/2007 | Sorge et al. ................ | 435/6 |
| 2008/0026387 A1 * | 1/2008 | Firmin et al. .............. | 435/6 |
| 2009/0192047 A1 * | 7/2009 | Parr et al. ................... | 506/9 |

FOREIGN PATENT DOCUMENTS

| | | |
|---|---|---|
| EP | 0 878 554 A2 | 11/1998 |
| WO | WO 0181631 A1 | 11/2001 |
| WO | WO 02/029085 | * 11/2002 |

OTHER PUBLICATIONS

Lyamichev et al., Structure-specific endonucleolytic cleavage of nucleic acids by eubacterial DNA polymerases. Science 260 : 778-783 (1993).*
Bi et al., Detection of known mutation by proof-reading PCR. Nucleic Acids Research 26 (12) : 3073-3075 (1998).*
Tyagi et al., Multicolor molecular beacons for allele disrimination. Nature Biotechnology 16 : 49-53 (1998).*
Rambaugh et al. Cleavage of substrates with mismatched nucleotides by flap endonuclease-1. Journal of Biological chemistry 274 (21) : 14602-14608 (1999).*
Lyamichev et al., Polymorphiosm identification and quantitative detection of genomic DNA by invasive cleavage of oligonucleotide probes. Nature Biotechnology 17 : 292-296 (1999).*
Saiki et al.Genetic analysis of amplified DNA with immobilized sequence-specific oligonucleotide probes PNAS 86(16) : 6230-6234 (1989).*
Gene Characterization Kits ; The Stratagene Catalog p. 39 (1988).*
International Search Report mailed Dec. 26, 2005 in the corresponding International Application No. PCT/ES2005/070093.

* cited by examiner

Primary Examiner — Ethan Whisenant
(74) Attorney, Agent, or Firm — Sughrue Mion, PLLC

(57) ABSTRACT

A nucleic acid detection method involving the direct generation of a measurable signal, by the action of an enzyme with 3'-5' nuclease activity, and the applications for it, the signal generated can be detectable and quantifiable and can be carried out in real-time, in this method, the nucleic acid is placed in contact with at least one oligonucleotide that does not hybridize perfectly with it, so that the enzyme will split it at the unpaired bases generating the signal, the oligonucleotide can be labeled.

23 Claims, 6 Drawing Sheets

Figure 7A. Profile of fluorescence emission obtained during reverse transcription coupled to gene amplification, of two samples in serum infected with HIV and of a negative "no-RNA" control.
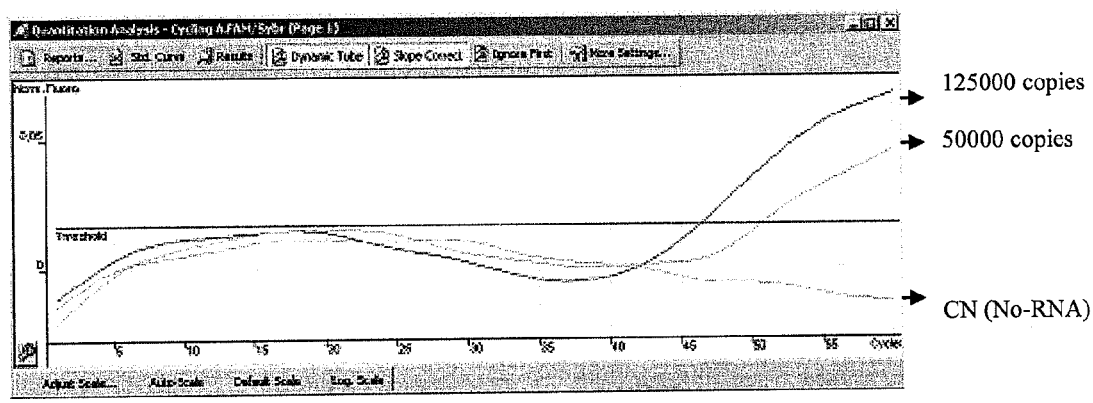
Figure 7B. Analysis by gel electrophoresis of products amplified in figure 7A.
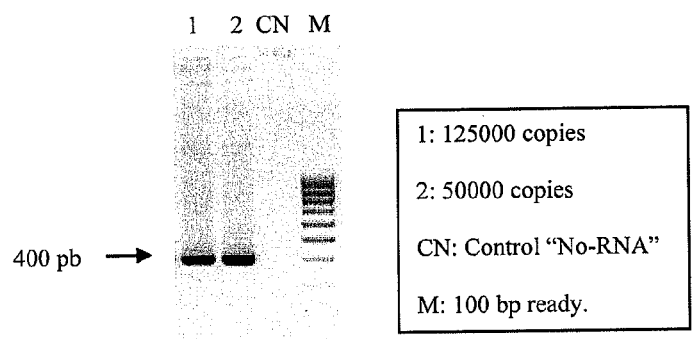
1: 125000 copies
2: 50000 copies
CN: Control "No-RNA"
M: 100 bp ready.

NUCLEIC ACID DETECTION METHOD INVOLVING THE DIRECT GENERATION OF A MEASURABLE SIGNAL

CROSS-REFERENCE TO RELATED APPLICATIONS

This application is a U.S. National Stage of application under 35 U.S.C. §371 of International Application No. PCT/ES2005/070093 (published as WO 2006/136621 A1), filed Jun. 16, 2005. Benefit of the filing date of this International Application is hereby claimed. This International Application is hereby incorporated by reference in its entirety.

DESCRIPTION

Object of the Invention

The present invention refers to a nucleic acid detection method involving the direct generation of a measurable signal, by the action of an enzyme with 3'-5' nuclease activity, and applications for it. The signal generated can be detected and quantified in real time.

The nucleic acid is placed in contact with one or more oligonucleotides that do not hybridize perfectly with it, so that the enzyme will split it into unpaired bases generating the signal.

The oligonucleotide can be labeled.

BACKGROUND OF THE INVENTION

Detection and quantification of nucleic acids are among the most important techniques in molecular biology and are rapidly evolving.

Basic classical techniques to analyze nucleic acids correspond to electrophoresis and probe hybridization that can be carried out in both the liquid and solid phase.

An important step in the development of nucleic acid manipulation techniques is the development of PCR (from the abbreviation Polymerase Chain Reaction).

The PCR technique (Saiki et al., *Science,* 230, 1350-1354 (1985), Mullis et al., North American patents U.S. Pat. No. 4,683,195, U.S. Pat. No. 4,683,202 y U.S. Pat. No. 4,800,159), permits the exponential amplification of nucleic acids.

This amplification is achieved by repeated cycles of denaturisation of the nucleic acid studied, by heat, binding complementary primers to two opposing regions of the nucleic acid to be amplified, and extension of the nucleic acid by the action of a polymerase enzyme. The repetition of successive cycles of this process results in exponential amplification of the nucleic acid.

In the PCR technique, polymerases are used to obtain amplification of the nucleic acid studied.

DNA polymerases catalyze the synthesis of nucleic acids, and in spite of the fact that all of them can polymerize nucleic acids in the 5'-3' region, there are differences among them in relation to the presence or absence of other characteristics, such as: exonuclease activity of the double helix, exonuclease activity of the single strand 3'-5', exonuclease activity of the double strand 3'-5', or reverse transcriptase activity.

The polymerases that present 3'-5' exonuclease activity, perform DNA replication with much better accuracy since they proofread the errors in the replicated bases (Brutlag, D. And Kornberg, A. J. Biol. Chem. (1972) 247:241-248). When DNA polymerases with 3'-5' exonuclease activity with proofreading activity are used in the replicator system, the DNA obtained includes a smaller proportion of base errors than replicas that do not use these types of enzymes (Chang, L. M. S., J. Biol.: Chem. (1977) 252:1873-1880.

Proofreading DNA polymerases with 3'-5' exonuclease activity are well known. Documents such as patent with publication no. U.S. Pat. No. 5,500,363, and the patent with publication no. U.S. Pat. No. 5,352,778, include a description of how to obtain and produce a thermostable recombinant polymerase with 3'-5' proofreading activity.

In the patent with publication number U.S. Pat. No. 6,489,150, the use of these types of DNA polymerases with 3'-5' proofreading activity is described for the synthesis of nucleic acids.

In the patent with publication number WO0181631, a method is described to analyze in a nucleic acid variable sites in the presence of a polymerase with 3'-5' exonuclease activity. This enzyme, in the case that one of the primers is not complementary to the target nucleic acid with the variable site, cuts the 3' end of the primer, releasing the marker of this primer, after which the presence or absence of this marker is analyzed. By this method, one of the sequences present in the mixture is amplified and/or selectively labeled. However, the process does not generate a detectable signal, thus analysis of the presence of the marker requires an additional analysis of the products generated.

A PCR variant has been developed, real-time PCR, in which the amplification and detection processes are produced simultaneously, without requiring any further operation. Moreover, the amount of DNA synthesized at each moment can be measured by fluorescence detection during the amplification, since the fluorescence emitted during the reaction is proportional to the amount of DNA formed. Hence, the kinetics of the amplification reaction can be determined and known at any moment (Higuchi R, Fokler C, Dollinger G, Watson R. Kinetic PCR analysis: Real-time monitoring of DNA amplification reactions. Bio/Technology 1993; 11: 1026-30).

Currently, most equipment related to real-time PCR technology corresponds to the so-called thermocyclers that incorporate a fluorescence reader and are designed to measure, at any time, the fluorescence emitted in each of the test-tubes in which the amplification has been carried out.

The fluorescence detection systems currently most used in real-time PCR, are:

Fluorescent intercalating agents (such as SYBR Green)

Hydrolysis probes that use the 5'-3' nuclease activity of the DNA polymerases (such as TaqMan probes and LNA probes)

Hairpin probes (such as those known as Molecular Beacons and Scorpion)

Hybridization probes (such as those known as FRET probes, TaqMan MGB probes and MGB Eclipse probes)

The compound known with the brand name of SYBR Green and protected with the North American patent with publication number U.S. Pat. No. 5,436,134, is a much used fluorescent intercalating agent. This compound is a derivative of cyanine that binds to the double stranded nucleic acid, emitting a fluorescent signal that increases proportionally as the PCR product increases.

In a similar way as these intercalating agents bind to the nucleic acid products of the PCR, they can also bind to primer-dimers and to other non-specific products, and can have non-specific amplification signals resulting in an overestimation of the concentration of the target to be labeled.

Other kinds of fluorescent labeling systems correspond to hydrolysis probes, such as that with the brand name TaqMan, described in the patent of the invention with publication number U.S. Pat. No. 5,723,591. These probes are bound to a fluoride reporter at the 5' end and a fluoride blocker or quencher at the 3'end. The Taqman probes, together with polymerases with 5'-3' exonuclease activity, are used to monitor amplification of the nucleic acids. When both fluorides are bound to the probe, the reporter is diminished by the quencher and no signal is emitted. The probe is joined to the nucleic acid strand to be amplified, when this nucleic acid is replicated the 5'-3' exonuclease activity of the DNA polymerase 5'-3' exonuclease, frees the 5' end of the probe where this is joined to the fluoride reporter, producing emission of a fluorescent signal.

Hairpin probes have inverted repeat sequences at their 5' and 3' ends, permitting a hairpin shaped structure to be formed owing to the complementarity of the two repeat inverted regions, in the absence of the target sequence. The internal sequence of the probe is complementary to the target sequence, so that in its presence, the hairpin structure opens, increasing the distance between the fluoride reporter and the fluoride quencher, so that the fluorescent signal is emitted.

Other known probes are the hybridization probes, the design of which involves the use of two specific oligonucleotide sequences as probes, each labeled with a different fluoride. The ends of the probe are complementary and usually the 3' end of one of them is the donor. When this molecule is excited by a light source it transfers its energy to the 5' end of the second probe, the acceptor molecule. The two probes are designed to hybridize in their specific targets so that both fluorides are in close proximity, so transfer of the resonance energy only occurs when both probes hybridize to the target, and are very close together.

There are other types of probe with a more limited and incipient use, such as the probes: "Resonsense", "Light-up", "HyBeacon", "LUX", "Yin-yang", "Amplifluor" etc.

The present invention provides a new method to detect and quantify nucleic acid by the action of an enzyme with 3'-5' nuclease activity.

DESCRIPTION OF THE INVENTION

The present invention refers to a method to detect specific sequences of DNA or RNA nucleic acids, by generating a detectable and/or quantifiable signal mediated by a 3'-5' nuclease activity. This method consists in placing the nucleic acid substrate to be identified in contact with at least one oligonucleotide, designed so that this oligonucleotide can hybridize with the nucleic acid substrate, leaving one or more bases unpaired at the 3' end of the oligonucleotide, or adjacent bases.

The double banded nucleic acid structure with unpaired bases at the 3' end of the oligonucleotide chain acts as the substrate for the 3'-5' nuclease activity also present that splits the unpaired bases of the oligonucleotide, and the bases are found in position 3' of the unpaired zone, generating a measurable signal.

This oligonucleotide can include a marker, either in one of the unpaired bases when the oligonucleotide/substrate hybrid is generated, or in a base at position 3' of the unpaired base in the duplex. Moreover, the oligonucleotide can carry additional markers at any number or position along the oligonucleotide chain.

The term marker, as used in the present invention, refers to any atom or molecule which can be used to give a detectable and/or quantifiable signal, which is joined to the oligonucleotide.

Markers can give a signal detectable by fluorescence, an electric signal, an electrochemical or magnetic signal, one detectable by radioactivity, colorimetry, gravimetry, X-ray diffraction or by absorption, enzymatic activity, chemoluminescence, luminous, or vibrational.

In a more specific aspect of the invention, the oligonucleotide chain presents a double labeling with a fluoride quencher and a fluoride reporter.

In a more specific embodiment of the invention, the fluoride quencher is at the 5' end of the oligonucleotide chain while the 3' end is labeled with a fluoride reporter.

In one embodiment of the method, oligonucleotides are used that do not incorporate any type of marker in their sequence, to perform assays by gravimetry. In these assays, the signal generated is not determined by splitting a labeled group, but by the mass difference produced when a base or group of bases is split off from the 3' end of the oligonucleotide measured by the 3'-5' nuclease activity.

In one embodiment of the invention, the 3'-5' nuclease activity is derived from a polymerase with proofreading activity.

Similarly, the 3'-5' nuclease activity, or the polymerase activity with proofreading activity can be resistant to incubations at high temperatures (thermostable enzymes) or may not (thermolabile enzymes).

In the method of the invention, the nucleic acid (DNA or RNA) can be derived from any complex sample that includes this type of molecule in its composition, such as sections or extensions of animal or plant tissue, cell cultures or biological material in general, food products, air, soil and water samples. Similarly, it can also derive from previously processed samples, such as in vitro transcription products (cDNA) or gene amplification products (PCR), isothermal amplification or have been generated in rolling-circle amplification systems. Finally, both the probe and the substrate, can appear in liquid solution, or in systems in which the probe or the substrate are fixed to solid supports, whatever their nature (membranes, glass, plastic or similar).

In one specific amplification of the present method, this can be used to detect and distinguish between nucleic acid sequences that differ in only one base change (SNPs). To do this, the design of the oligonucleotide is such that, as it hybridizes with the substrate sequence, the position of the relevant mutation is located at the 3' end of the oligonucleotide.

The sequence of this oligonucleotide should hybridize perfectly with the nucleic acid substrate that does not present the mutation and will, consequently, present an unpaired base at the 3' end when this hybridizes with the substrate sequence of the mutation. When hybridization takes place between the oligonucleotide and the substrate nucleic acid sequence that does not present the mutation, the oligonucleotide/nucleic acid substrate duplex is perfect, without any unpairing, and does not generate any substrate for the action of the 3'-5' nuclease activity, thus the oligonucleotide remains intact and no signal is generated.

By contrast, when the DNA substrate that presents the mutation hybridizes, the nucleic acid/oligonucleotide duplex is not perfect, leaving an unpaired base at the 3' end of the oligonucleotide that is recognized by the activity of the 3'-5' nuclease present in the mixture.

By this activity, the unpaired base is spilt from the oligonucleotide chain, releasing a detectable signal.

In one application of the method, this is used to detect the existence of mutations in encoding codons of the nucleic acid.

For this purpose, the design of the oligonucleotide is such that the codon to be analyzed is located at the 3' end of the oligonucleotide. The sequence of this oligonucleotide should be perfectly complementary to the non mutant nucleic acid substrate, which need not be detected. In the presence of substrate nucleic acids with mutations in this codon, the oligonucleotide/nucleic acid substrate duplex presents an unpairing of mutated bases at the 3' end of the oligonucleotide, which is transformed into substrate for the 3'-5' nuclease activity.

By using this method changes can be detected in any of the three bases that constitute the encoding codon, both in the case of punctual mutations at any position, and also in the case of double or triple mutations in this codon.

In this application, the labeled oligonucleotide can present additional changes in its sequence, such as the joining of bases by non-phosphodiester bonds or the inclusion of spacers with the aim of protecting some positions of the oligonucleotide from the activity of the 3'-5' nuclease, in the case that these positions represent conservative mutations.

In one embodiment of the invention, the oligonucleotide or oligonucleotides operate simultaneously to generate the signal mediated by 3'-5' nuclease activity, and as a primer of nucleic acid extension reactions, both in primer extension and in polymerase activity-mediated amplification, so that nucleic acid extension occurs simultaneously to signal generation.

For this purpose, the DNA substrate is placed in contact with the oligonucleotide, a mixture of dNTPs required for the extension reaction of the nucleic acid, an enzyme with 3'-5' nuclease activity and an enzyme with polymerase activity, together with the appropriate buffers for the enzymatic activities.

In the case of PCR type gene amplification reactions an additional primer is required of opposite polarity that could be a reference oligonucleotide or present unpaired bases in the 3' region when it hybridizes with substrate DNA. With the application of a PCR system with two primers susceptible to proofreading by 3'-5' nuclease activity, the system's specificity can be increased. Finally, this second primer can also be labeled, generating a signal identical to or different from the one generated by the first primer.

In this application of the invention, and given that this is coupled with a catalytic reaction mediated by a 3'-5' nuclease activity and a polymerization reaction mediated by a polymerase activity, the enzyme used can be a polymerase with 3'-5' nuclease proofreading activity.

Similarly, and since in the primer extension reaction, and especially in the PCR reaction, the application of successive heating/cooling cycles is required, the enzyme can be a thermostable polymerase with 3'-5' nuclease proofreading activity.

In this application, the design of the labeled oligonucleotide is such that this hybridizes with the DNA substrate to be detected, except for at the 3' end of the oligonucleotide, or in bases adjacent to this end. As the oligonucleotide hybridizes with the substrate DNA, a duplex with unpaired bases is generated at the 3' terminal of the oligonucleotide. The unpaired bases of the oligonucleotide are split by the activity of the 3'-5' nuclease, releasing the marker that was joined to these bases. As these bases are split, the shortened oligonucleotide now hybridizes perfectly with the DNA substrate, and presents a 3' end with a free OH group, thus this oligonucleotide can now serve as a primer of nucleic acid chain extension mediated by the polymerase activity.

In this type of assay, the oligonucleotide used to generate the signal/primer of nucleic acid synthesis may or may not present additional modifications that block the hydroxyl group of the final base in position 3', to protect the hydrolysis of some positions, or with the aim of stopping the extension reaction of the unmodified oligonucleotide by the activity of the 3'-5' nuclease.

Hence, in primer extension reactions, or PCR of SNPs, the use of oligonucleotide with an unblocked 3' end permits the extension or amplification both of the DNA to be detected, and the DNAs that do not need to be identified.

However, only the extension or amplification of the DNA in question generates the detectable signal mediated by the 3'-5' nuclease activity.

In contrast, the use of oligonucleotides with a modified 3' terminal, blocks both the amplification and the emission of the signal of the sequence that does not have to be detected.

In a specific embodiment of the invention, the oligonucleotide in nucleic acid extension or amplification systems functions only as a signal generator mediated by 3'-5' nuclease activity, and does not function as a primer of the reaction.

In this system, the oligonucleotide operates as a probe, binding to the nucleic acid of interest and generating a signal mediated by the 3'-5' nuclease activity. Consequently, the system requires the presence of two or more primers of the nucleic acid extension reaction, the labeled oligonucleotide that will act as a probe, a polymerase 3'-5' nuclease proofreading activity, a polymerase with chain displacement activity and/or 5'-3', nuclease activity and a mixture of dNTPs and the appropriate buffers. Alternatively, the oligonucleotide primers that prime DNA synthesis may or may not present punctual unpaired bases at the 3' end on hybridization with the substrate.

If the enzyme that presents chain displacement activity also presents 5'-3' nuclease activity, to ensure that the signal generated proceeds from the 5'-3' nuclease activity of the polymerase added to the reaction, additional modifications must be introduced in the oligonucleotide. To inhibit the 5'-3' activity of this type of polymerase, several strategies can be followed, such as the inclusion of a palindromic sequence in the 5' terminal of the oligonucleotide, or the chemical modification of its 5' end, such as phosphorylation, addition of inverse polarity bases by 5'-5' bonds.

Finally, to prevent extension of the oligonucleotide used as a probe, this should also present additional modifications at its 3' end, by any technique that blocks the OH free end, such as phosphorylation or addition of any molecule linked to this group.

The simultaneous use of oligonucleotides with different markers permits the multiplexation of amplification reactions or the analysis of different changes in the amplified sequence.

In a specific application, the method is used in gene amplification reactions in which the oligonucleotide labeled with a fluoride quencher is located at the 5' end of the oligonucleotide chain while the 3' end is labeled with a fluoride reporter. In this application, the amplification reaction is carried out coupled to an instrument that can monitor fluorescence emission in each amplification cycle permitting an amplification assay to be carried out in real-time. This application can be done using oligonucleotides that function simultaneously as signal generators and as primers for chain elongation, or with oligonucleotides that function as pure probes, without participating as primers of the elongation reaction.

In one embodiment of the invention, direct signal generation is used to detect a specific sequence in a hybridization system in the absence of a polymerization reaction. This method requires a high concentration of the nucleic acid substrate to be identified and consists in placing the nucleic acid substrate in contact with the labeled probe and the 3'-5' nuclease activity, and this, in turn, could correspond to a polymerase with 3'-5' nuclease proofreading activity. The mixture does not contain dNTPs, since chain elongation is not carried out. This method can be carried out in a single hybridization/catalysis step, or in successive cycles in which in one temperature increment step the oligonucleotide and nucleic acid substrate are separated and in a subsequent incubation step at a lower temperature, the nucleic acid substrate hybridizes with a new probe.

There is, therefore, a linear increase in the signal in each cycle of the process. In a special embodiment, an oligonucleotide is used marked with a fluoride quencher at the 5' end of the chain, while the 3' end is marked with a fluoride reporter. In this application, the cyclic hybridization/catalysis is performed in an instrument that can monitor fluorescence emission in each amplification cycle permitting the detection assay to be performed in real-time.

The reagents used in this invention can be presented as nucleic acid detection kits. The kits include the oligonucleotides with a sequence complementary to the ones we wish to detect with one or more non-complementary bases at the 3' end of the chain. The oligonucleotides can be labeled, if they are not labeled specific marker reagents can also be included in the kit.

The kits also include an enzyme with 3'-5' nuclease activity, such as the polymerase with 3'-5' proofreading activity (pfu), or another. The kits can contain additional enzymes with polymerase activity.

The kit can include at least one oligonucleotide primer of the nucleic acid that may or may not be labeled.

The kit can also contain other reagents required to carry out the detection and the materials required for the amplification, for example, buffer, dNTPs, magnesium ions, and instructions to carry out the assay.

DESCRIPTION OF THE DRAWINGS

This descriptive report is accompanied by a set of figures that serve to illustrate a preferable embodiment of the invention, but in no way restrict its application.

FIG. 1A) pMTB-Control, FIG. 1B) Mutant 1F, FIG. 1C) Mutant 1P and FIG. 1D) Mutant 2 PF. The central sequence of each diagram shows the sequence of the DNA substrate. The top sequence corresponds to the primer IS and the bottom sequence to the primer IS-INV. Boxes are used to show the unpaired bases between the probes and the DNA substrate.

FIG. 2A) Amplification mixture with IS probe and DNA pfu polymerase; FIG. 2B) Amplification mixture with IS-INV probe and pfu DNA polymerase; and FIG. 2C) Amplification mixture with IS-INV probe and DNA polymerase 5'-3' exonuclease polymerase.

FIG. 3A shows the fluorescence graph versus the number of cycles. The top part of the graph shows the amplification profiles obtained when using the IS-INV probe as a source of fluorescence, the bottom part shows the profiles obtained using intercalating fluoride SYBR Green. FIG. 2B shows the agarose gel analysis in the amplified products obtained. Lane 1 corresponds to a $10^{-3}$ dilution, lane 2 to a $10^{-6}$ dilution, lane 3 to a $10^{-8}$ dilution and lane 4 to a No-DNA negative control, lane M corresponds to a 100 bp Ladder. The lanes on the right correspond to the assay with SYBR Green I, and on the left to the IS-INV probe.

FIG. 7A shows a profile of fluorescence emission obtained during reverse transcription coupled to gene amplification, of two samples in serum infected with HIV and of a negative "no-RNA" control.

FIG. 7B shows analysis by gel electrophoresis of products amplified in FIG. 7A.

PREFERRED EMBODIMENT OF THE INVENTION

Example 1

Amplification assay in real time using oligonucleotides with double fluorescent labeling as primers of the amplification reaction in the presence of pfu DNA polymerase activity.

The amplification and detection of fluorescence was assayed in an amplification system in real time using double-labeled primers in the presence of DNA polymerase pfu activity, on substrate DNAs with different levels of unpaired bases in the region of primer hybridization. In this, and in the other examples of this invention, the oligonucleotides that carry the marker and have been designed to present unpaired bases at the 3' terminal or adjacent bases on hybridization with the nucleic acid substrate, which makes them, consequently, susceptible to partial degradation and to generate a signal mediated by the 3'-5' nuclease activity included in the reaction mixtures, are given the generic name of Lion probes.

For this assay, amplification was done of a conserved region of IS6110 of the *Mycobacterium tuberculosis* (MTB). The substrate DNAs and primers and the probes used are shown below:

Substrate DNAs.

A control plasmid (pMTB-Control) was obtained by cloning a 335 bp fragment of the IS6110 region of *Mycobacterium tuberculosis* (MTB) in the pBlueScript SK(+) plasmid.

Three mutant sequences (gene amplification products) of 310 bp of the IS6110 region cloned in the control plasmid (pMTB-Control) described previously.

Figure 1A:
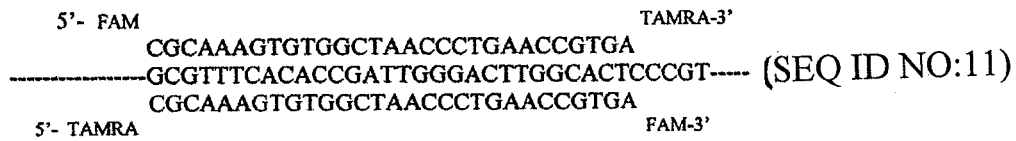
FIGS. 1A, 1B, 1C, and 1D, show diagrams of the hybridization of the oligonucleotides IS and IS-INV having the nucleotide sequence of SEQ ID NO:1 with the DNA substrate (SEQ ID NO:11).
Figure 1B:
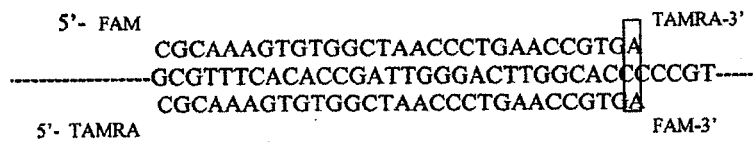
Figure 1C:
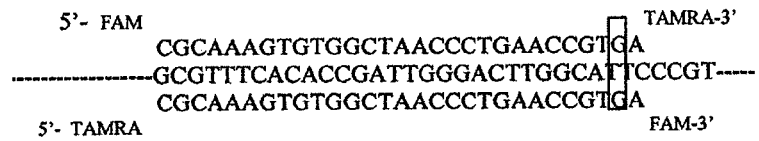

Mutant 1P: mutation in the penultimate base of the hybridization region with the primers Lion probe IS and Lion probe IS-INV. This generates an unpaired base at the last base of the 3' end of both primers when it hybridizes with them, as can be seen in FIG. 1C.

Mutant 1F: mutation in the last base of the zone of hybridization between the primers Lion probe IS and Lion probe IS-INV. It produces an unpaired base at the 3' end of both primers on hybridization with them, shown in FIG. 1B.

Figure 1D:
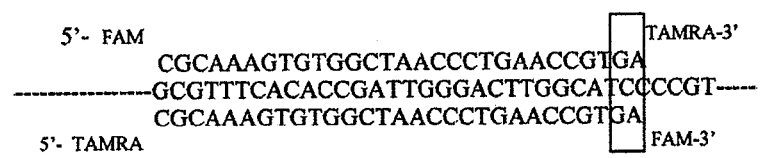

Mutant 2 PF: mutation of the last two bases of the hybridization region with the primers Lion probe IS and Lion probe IS-INV. It generates unpairing of the last two bases of the 3' end of both primers when it hybridizes with them, as can be observed in FIG. 1D.

Amplification Primers.

The following oligonucleotides will be used as primers of the amplification reactions:

Lion probe IS. Forward primer with nucleotide sequence of SEQ ID NO:1 that presents double labeling at its ends. The 5' end is labeled with FAM (6-carboxy-fluoresceine) and the 3' end with TAMRA (6-carboxytetramethyl-rodamine), a FAM blocker. It hybridizes perfectly with the plasmid control sequence, and presents unpaired bases at the 3' end with mutant DNAs 1P, 1F and 2 PF.

Lion probe IS-INV. Forward primer with nucleotide sequence identical to that of primer Lion probe IS (i.e., SEQ ID NO:1) but with inverted end labels. Hence, the 5' end is labeled with TAMRA and the 3' end with FAM. Like the primer IS, it hybridizes perfectly with the plasmid control sequence and presents unpaired bases at the 3' end with mutant DNAs 1P, 1F and 2 PF.

Primer MT2 (SEQ ID NO:2, 5'-CATCGTGGAAGCGAC-CCGCCAGCCCAGGAT-3'). Reverse primer, which hybridizes perfectly with the sequences of the four previously described substrates. This primer was used as a reverse primer in all the experiments studied in this example.

To verify the effect of the orientation of the fluorescent labels in the probe used as primer, two alternative mixtures were tested; one using the IS probe, and the other using the IS-INV probe. The amplification mixtures were as follows:

Amplification mixture with Lion probe IS and pfu DNA polymerase: performed with the Biotools Pfu DNA polymerase kit (Biotools B & M Labs, Madrid, Spain), including in the mixture 0.1 u/µl of Pfu DNA polymerase, reaction buffers, a mixture of dNTPs, Lion probe IS (0.3 µM final) and oligonucleotide MT2 (0.5 mM final), with a final reaction volume of 20 µl.

Amplification mixture with Lion probe IS-INV and pfu-DNA polymerase: performed with the kit Biotools Pfu DNA polymerase (Biotools), including in the mixture 0.1 u/µl of Pfu DNA polymerase, the reaction buffers, a mixture of dNTPs, Lion probe IS-INV (0.3 µM final) and oligonucleotide MT2 (0.5 mM final), with a final reaction volume of 20 µl.

Amplification mixture with Lion probe IS-INV and DNA polymerase 5'-3' exonuclease: performed with the kit Biotools DNA polymerase (Biotools), including in the mixture 0.1 u/µl of DNA polymerase 5'-3' exonuclease, reaction buffers, a mixture of dNTPs, Lion probe IS-INV (0.3 µM final) and oligonucleotide MT2 (0.5 mM final), with a final reaction volume of 20 µl.

With each mixture the amplification of pMTB-Control plasmid was assayed (5000 copies) and of the mutants 1P, 1F and 2 PF (direct PCR product), and a no-DNA control.

The amplification reaction was performed in a real-time amplification system SmartCycler II (Cepheid) using the following amplification cycles:

In a first step, the temperature was maintained for 360 s at 95.0° C.

In a second step, the cycle was repeated 45 times:
Temperature at 95.0° C. for 5 s.
Temperature at 57.0° C. for 5 s.
Temperature at 60.0° C. for 40 s.

Amplification reaction course was monitored in real-time by reading the fluorescence level in the FAM channel, measured in the incubation step at 60° C. Similarly, the amplified products were analyzed in 1.5% agarose gel stained with ethidium bromide. The results are shown in FIG. 2.

Figure 2A:
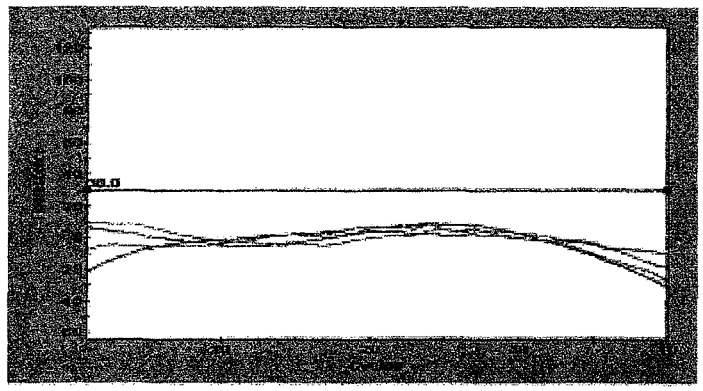
FIG. 2A, 2B, 2C, show on the left the amplification results in real-time of different DNA substrates on fluorescence graphs (FAM channel) relative to the number of cycles in the different cases. On the right of these figures, analysis in agarose gel is shown of the amplified products at the end of the process.
Figure 2A:
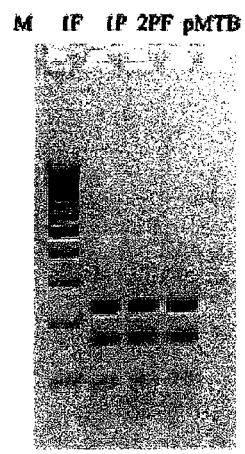
Figure 2B:
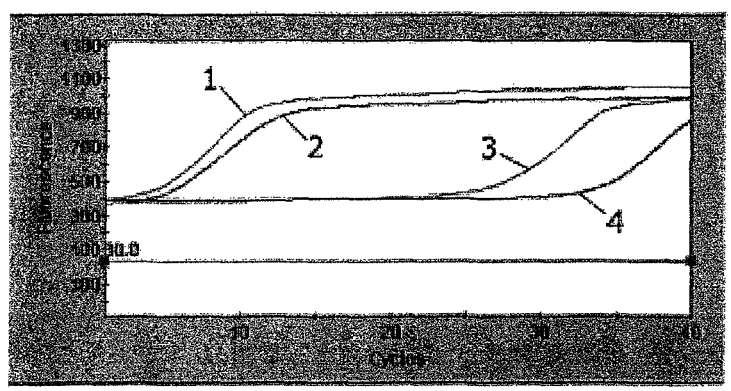
Figure 2B:
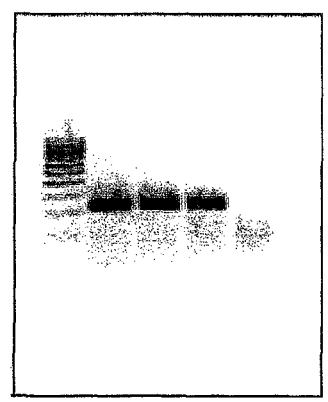
Figure 2C:
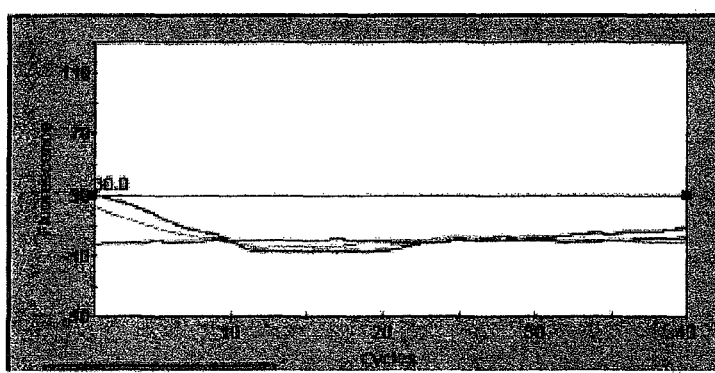
Figure 2C:
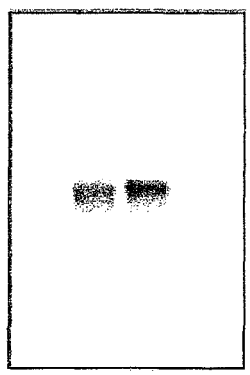

All the samples amplified with the Lion probe IS (labeled 5' FAM - - - 3' TAMRA) were negative in the fluorescence curves generated during the amplification process, as shown in FIG. 2A. In contrast, all the samples amplified with the Lion probe IS-INV and pfu-DNA polymerase were positive, with high fluorescence levels. Fluorescence appeared very quickly in the case of the amplification of substrate mutants DNAs, 1F (1), 1P (2) (very low threshold values) and much later in the pMTB control plasmid amplification (3) and no-DNA control (4), as shown in FIG. 2B. Finally, the samples amplified with DNA polymerase 5'-3' exonuclease (that does not have 3'-5' exonuclease activity) and the Lion probe IS-INV were negative in all cases, showing that the signal obtained in the pfu assays were due to the presence of this exonuclease activity.

On the contrary, analysis in agarose gel of the amplified products demonstrated that both the DNA mutant samples amplified with the Lion probe IS, and those amplified with the Lion probe IS-INV, using in both cases the pfu DNA polymerase were positive, with the appearance of an amplification band of the expected size (220 bp) in all cases. By contrast, the samples amplified with pMTB and no-DNA controls were negative, with the appearance of low molecular weight bands corresponding to primer-dimer.

The results obtained confirm that the 3'-5' exonuclease activity of the pfu DNA polymerase is effective at amplifying and generating fluorescent signals using double labeled probes (fluoride and blocker) that present unpaired bases at the 3' end of the primer with the DNA substrate. However, the orientation of the labels is essential when generating this fluorescent signal. Hence, the use of probes with fluoride in position 5' and the blocker in position 3' are effective in the amplification reaction, but not in generating the fluorescent signal. This can be explained by the fact that although the blocker is removed from position 3' when the pfu performs its proofreading function, the fluorescent label remains integrated in the 5' end of the amplified product, and is blocked by the DNA sequence. On the contrary, the use of probes with fluoride bound to the 3' end and the blocker at the 5' end, produces direct release of the fluoride as the pfu performs its proofreading function, permitting the effective emission of fluorescence.

The appearance of fluorescent signals in the no-DNA samples associated with the observation of dimerisation bands of primers in the agarose gels, suggest that in this system although the probes used as primer in combination with the pfu present a totally different action mechanism, they generate similar results to those obtained using intercalating fluorides such as SYBR Green. This is because the release of fluorescence mediated by the 3'-5' exonuclease activity of the pfu is effective provided that a hybridization takes place with an unpaired base at the 3' end of the probe, independently of the origin of the DNA substrate.

Example 2

Comparison of the fluorescence emission efficacy in real-time amplification systems with pfu DNA polymerase, using oligonucleotides with fluorescent double labeling (Lion probes) as primers of the reaction or intercalating fluorides (SYBR Green).

Since in Example 1 it was observed that the use of DNA amplification systems with pfu DNA polymerase using, as a primer of the reaction, a fluorescent double labeled probe in the presence of substrates that produce unpaired bases at the 3' end of the probe, generates similar fluorescence results to those obtained with intercalating fluorides, such as SYBR Green, a comparative assay was performed of both systems.

To do this, an amplification system of MTB similar to that used in Example 1 is used. The substrate and primer DNAs and the probes used are shown below.

DNA Substrate.

Mutant 2 PF: mutation in the last two bases of the zone of hybridization with the Lion probes IS and IS-INV. This generates an unpairing of the last two bases of the 3' end of both primers as it hybridizes with them.

Amplification primers.

The following oligonucleotides were used as primers of the amplification reaction:

Lion probe IS-INV. Fluorescent double labeled probe (5' TAMRA --- FAM 3'). Partially hybridizes with the sequences of the Mutant 2 PF sequence substrate, presenting an unpairing of the last two bases of the 3' end of the primer as this hybridizes with the substrate.

Primer ISFOW (SEQ ID NO:3, 5'-CGCCAACTACGGT-GTTTACGG-3'). Forward primer that hybridizes perfectly (100% homology) with the DNA sequence of the Mutant 2 PF DNA substrate.

Primer ISREV (SEQ ID NO:4, 5'-CGACACATAGGT-GAGGTCTGCTA-3'). Reverse primer that hybridizes perfectly (100% homology) with the DNA sequence of the Mutant 2 PF DNA substrate.

Two alternative reaction mixtures were prepared:

Amplification mixture with Lion probe IS-INV y pfu-DNA polymerase: carried out with the Biotools Pfu DNA polymerase kit (Biotools), including in the mixture 0.1 u/µl of Pfu DNA polymerase, the reaction buffers, a mixture of dNTPs, Lion probe IS-INV (0.3 µM final) and oligonucleotide ISREV (0.5 mM final), with a final reaction volume of 20 µl.

Amplification mixture with SYBR-Green and pfu-DNA polymerase: carried out with the Biotools Pfu DNA polymerase kit (Biotools), including in the mixture 0.1 u/µl of Pfu DNA polymerase, the reaction buffers, a mixture of dNTPs, oligonucleotide ISFOW (0.5 µM final), oligonucleotide ISREV (0.5 mM final) and SYBR Green I (Sigma-Aldrich Corp, St. Louis, Mo., USA), where the final reaction volume is 20 µl.

With each mixture, amplification of serial dilutions was assayed (undiluted DNA and dilutions of $1/10^3$, $1/10^6$ and $1/10^8$) and a no-DNA control.

The amplification reaction was carried out in a SmartCycler II (Cepheid) real-time amplification system using the following amplification cycles:

In a first step the temperature was maintained for 360 s at 95.0° C.

In a second step the following cycle was repeated 45 times:
Temperature at 95.0° C. for 5 s.
Temperature at 57.0° C. for 5 s.
Temperature at 60.0° C. for 40 s.

The course of the amplification reaction was monitored in real-time by reading the fluorescence level in the FAM channel in each amplification cycle, measured in the incubation step at 60° C. Similarly, the amplified products were analyzed in 1.5% agarose gel stained with ethidium bromide. The results are shown in FIG. 3A, and 3B.

Figure 3A:
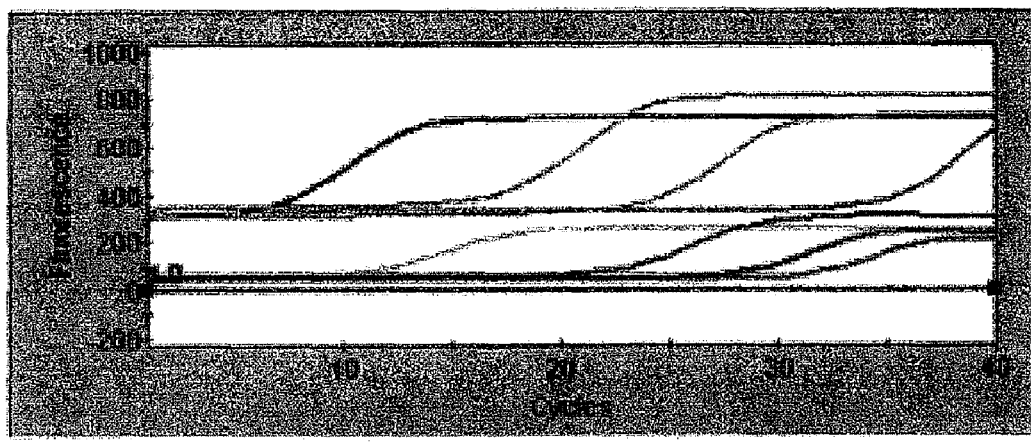
FIGS. 3A and 3B show the results of the comparative amplification assay in real-time using the IS-INV probe as a source of fluorescence in the presence of pfu DNA polymerase, or the intercalating fluoride SYBR Green I in the presence of pfu.
Figure 3B:
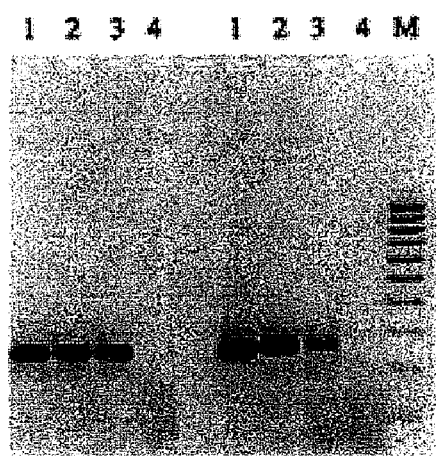

As shown in FIG. 3A, all the samples analyzed, both in the presence of Lion probe IS-INV, and those amplified in the presence of SYBR Green were positive. However, appearance of the fluorescence signal was faster in the samples amplified with the IS-INV probe (top half of the graph) than in samples amplified with SYBR Green (lower half of the graph). Hence, the samples amplified with Lion probe IS-INV presented a mean reduction in Ct values (threshold cycle) compared to the same samples analyzed in the presence of SYBR Green of approximately 6,155 cycles. On the other hand, although the no-DNA control was positive in both assays, in the sample amplified with Lion probe IS-INV the fluorescence curve appeared 2.35 cycles later than in the control amplified with SYBR Green.

Table 1 of the results shows the Ct values obtained in the samples amplified with probe IS-INV and those obtained with SYBR Green.

TABLE 1

| Sample | Ct |
|---|---|
| Mutant 2PF, dilution $10^{-3}$, (A1) | 8.23 |
| Mutant 2PF, dilution $10^{-6}$, (A2) | 16.39 |
| Mutant 2PF, dilution $10^{-8}$, (A3) | 23.21 |
| No DNA, (A4) | 34.33 |
| Mutant 2PF, dilution $10^{-3}$, (A5) | 12.23 |
| Mutant 2PF, dilution $10^{-6}$, (A6) | 23.07 |
| Mutant 2PF, dilution $10^{-8}$, (A7) | 28.92 |
| No DNA, (A8) | 31.96 |

A1, A2, A3 and A4: Samples amplified with probe IS-INV. A5, A6, A7 and A8: Samples amplified with SYBR-Green.

The mean delay of the Ct values of the samples amplified with SYBR Green compared to the samples amplified with probe IS-INV was calculated as the arithmetic mean of the differences in Ct obtained in each dilution analyzed.

Mean delay=[(A5–A1)+(A6–A2)+(A7–A3)]/3=5.46 cycles

The safety margin of each reading was calculated as the difference between the CT value of the no-DNA control and the Ct value of the weakest dilution analyzed (dil $10^{-8}$).

Margin in samples amplified with IS-INV probe: A4–A3=11.12 cycles

Margin in samples analyzed with SYBR Green: A8–A7=3.04 cycles

As shown in FIG. 3B, analysis of the products amplified in 1.5% ethidium bromide stained agarose gel, confirmed the presence of amplification bands of the expected size in all the samples of DNA amplified, and the absence of bands from the no-DNA controls, independent of the system used to generate the fluorescence (Lion Probe IS-INV or SYBR Green I).

The results obtained indicate that although use of double labeled probes as primers in the presence of pfu DNA polymerase generates similar results to those obtained using intercalating fluorides such as SYBR Green, the new method improves both the sensitivity, and potentially the specificity of the detection. Hence, the earliest values of fluorescence appearance, and the highest values of fluorescence obtained indicate a better sensitivity for the system. On the other hand, the combination of reduced CT values of the amplified samples and the delayed appearance of the fluorescent signal in no-DNA controls increases the safety range for detection of a given signal in comparison with SYBR Green. Hence, the difference in cycles between the last sample detectable and the primer-dimer signal in the experiment with IS-INV probe was 11.8 cycles per 3.3 cycles in the amplification experiment with SYBR Green.

Example 3

Confirmation of the Absence of 3'-5' Exonuclease Activity of the pfu on Fluorescently Labeled ssDNA Probes With the aim of guaranteeing that the fluorescent signal obtained in the systems assayed in examples 1 and 2 is not due to a degradation not dependent on the labeled probes mediated by the 3'-5' exonuclease activity of the pfu, incubation assays with the Lion probe IS-INV were carried out with pfu in the absence of DNA substrate. For this purpose, two alternative reaction mixtures were prepared:

A.—A reaction mixture with all the amplification reagents, except for additional primers. The incubation mixture therefore had the following composition: Performed with the kit Biotools Pfu DNA polymerase (Biotools), including in the mixture 0.1 u/µl of pfu DNA polymerase, the reaction buffers, a mixture of dNTPs and Lion probe IS-INV (0.3 µM final), giving a final reaction volume of 20 µl in all cases.

B.—Reaction mixture with all the amplification reagents, except for additional primers and dNTPs. The incubation mixture, therefore, presents the following composition: Performed with the Biotools Pfu DNA polymerase kit Biotools), including in the mixture 0.1 u/µl of Pfu DNA polymerase, the reaction buffers and Lion probe IS-INV (final 0.3 µM), with a final reaction volume of 20 µl in all cases.

The generation of a fluorescent signal in both reaction mixtures was assayed by duplicate in an absence of DNA substrate. The incubation conditions used were identical to those used during an amplification assay. Therefore, the amplification assay was carried out in a SmartCycler II (Cepheid) amplification system in real-time using the following temperature cycles:

In a first step, the temperature was maintained for 240 s at 95.0° C.

In a second step, the following cycle was repeated 40 times:
Temperature at 95.0° C. for 10 s
Temperature at 58.0° C. for 20 s
Temperature at 68.0° C. for 60 s
Fluorescence levels were monitored in the FAM channel in each of the incubations at 68° C. during the entire process.

Figure 4:
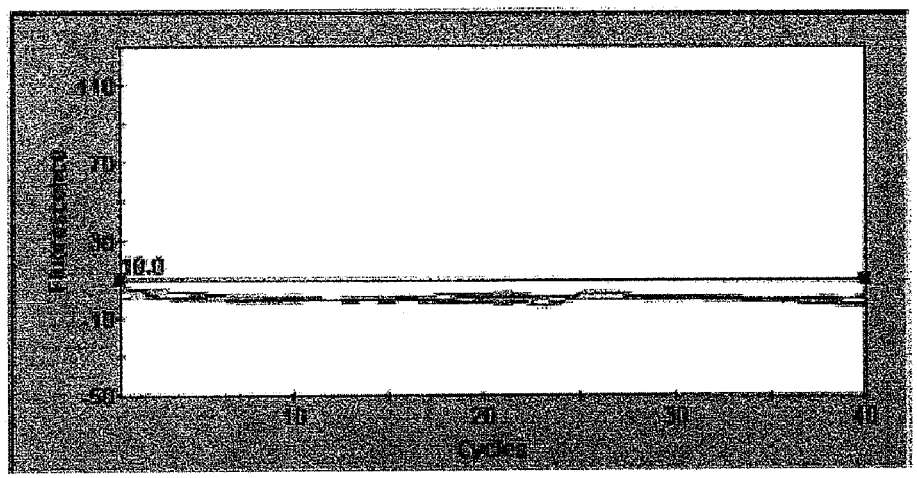
FIG. 4 shows the amplification results in real time on a graph of fluorescence versus the number of cycles, corresponding to example 3 of the present invention.

As shown in FIG. 4, a fluorescent signal was not obtained in any case during the incubation process, guaranteeing as a result, that the fluorescent signals obtained during the assays are not caused by the degradation of ssDNA probes with double labeling, owing to the 3'-5' exonuclease activity of the pfu DNA polymerase in a degradation mechanism independent of the substrate.

Example 4

Demonstration of the Absence of Contaminant 5'-3' Exonuclease Activity

In order to ensure the total absence of possible contaminant 5'-3' exonuclease activities in the preparation of pfu DNA polymerase that could affect interpretation of the results obtained, an amplification/detection assay was performed with TaqMan probes that require the presence of 5'-3' exonuclease activity to generate a fluorescent signal.

The experimental model used in this example is an amplification and detection system with TaqMan probe of a conserved region of the coding region of the human cytomegalovirus polymerase (CMV). The substrate DNAs and primers and probes used are described below:

Substrate DNA.

A plasmid (pCMV) obtained by cloning a conserved fragment of 350 base pairs (bp) of the coding region of the cytomegalovirus polymerase (CMV) in the pBlueScript plasmid SK(+).

Amplification Primers and Fluorescent Probes.

Primer CMVF (SEQ ID NO:5, 5'-GATAGACACACACT-GCAAA-3'). Forward primer that hybridizes perfectly (100% homology) with the region of the CMV genome cloned in the previously described plasmid pCMV.

Primer CMR (SEQ ID NO:6, 5'-GGTGGGACCTAT-TCGT-3'). Reverse primer that hybridizes perfectly (100% homology) with the region of the CMV genome cloned in the pCMV plasmid described previously.

CMV probe (SEQ ID NO:7 5'-TTCACACCTACGATCA-GACGGA-3'). TaqMan probe with double fluorescent labeling (5' FAM - - - - TAMRA 3') that hybridizes perfectly (100% homology) with an internal region of the product amplified with the combination of CMVF/CMVR primers described previously.

Serial 1/10 dilutions of the plasmid pCMV (range 5000-50 copies/reaction), were analyzed, and also a negative "no-DNA" control, using as primers CMVF and CMVR, and including the TaqMan probe with double fluorescent CMV-Probe labeling as a detection system. This probe, in the presence of a DNA polymerase with 5'-3' exonuclease activity (like the Taq polymerase) operates as a Taqman type hydrolysis probe. Both the amplification primers, and the hydrolysis probe present a perfect hybridization with the DNA substrate sequence analyzed. The amplification assays were performed in parallel with a DNA polymerase 5'-3' exonuclease enzymatic activity and pfu DNA polymerase, both produced by Biotools B&M Labs, LTD, and an exo Taq polymerase activity—(Clontech).

The reaction mixtures have the following composition: A mixture containing dNTPs, primer CMVF (0.5 µM), primer CMVR (0.5 µM) and probe CMV (0.3 µM). For polymerase activity, different enzymes were added in each experiment: 5'-3' exonuclease+DNA polymerase (Biotools DNA polymerase), Taq DNA polymerase exo—(Titanium Taq DNA polymerase. Clontech) or Pfu DNA polymerase (Biotools), adding in all cases 0.1 u/µl of enzyme, and a supplementing the reaction with specific buffers for each enzyme. The final reaction volume was 20 µl in all cases.

The amplification reaction was carried out in a SmartCycler II (Cepheid) amplification system in real-time using the following amplification cycles:

In a first step, the temperature was maintained for 360 s. at 95.0° C.

Figure 5A:
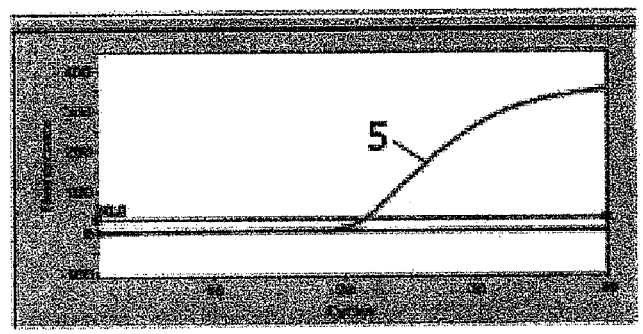
FIG. 5A shows the amplification results in real time, on a graph of fluorescence versus number of cycles, corresponding to example 4 of the present invention and in FIG. 5B, analysis in agarose gel of the amplified products obtained at the end of the process. In the agarose gel, the five lanes on the right correspond to the PCR results without a probe and the five lanes on the left to the PCR results with probe, represented by M: ladder 100 bp, 2: DNA pol 5'-3' exo +, 3:Taq polymerase exo-, 4: "no DNA" control.

In a second step the following cycle was 45 times:
Temperature at 95.0° C. for 5 s
Temperature at 57.0° C. for 5 s
Temperature at 60.0° C. for 40 s As shown in FIG. 5A, evolution of the amplification reaction was monitored in real time taking the reading in each amplification cycle of the fluorescence level in the FAM channel, measured in the incubation step at 60° C. Likewise, the amplification products were analyzed in 1.5% ethidium bromide stained agarose gel giving the results shown in FIG. 5B.

Figure 5B:
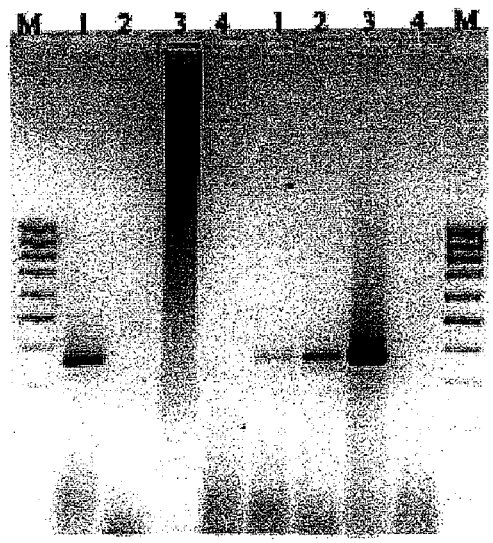

A fluorescent signal was only observed in the samples amplified with DNA polymerase 5'-3' exonuclease, which were in contrast negative for all the samples amplified with pfu or Taq DNA polymerase Exo—(5) (FIG. 5A). These results were confirmed by analyzing the products amplified in agarose gel observing amplification bands of the expected size in the samples treated with DNA polymerase 5'-3' exo-nuclease+and the total absence of these bands in the samples treated with pfu DNA polymerase or Taq Exo—(FIG. 5B).

These results confirm the expected behavior in the amplification systems assayed with both enzymes:

A.—The absence of fluorescence signal in the samples amplified with pfu DNA polymerase shows that the probe does not degrade during the amplification process, guaranteeing in this way the absence of 5'-3' exonuclease activities in the preparation of assayed pfu. By contrast, generation of the fluorescent signal was clearly detectable in the samples amplified with a DNA polymerase with 5'-3' exonuclease activity.

B.—The absence of amplification bands in the samples treated with pfu, shows that the probe used and that hybridizes perfectly with the substrate DNA, does not suffer degradation of the bases situated at position 3' so the blocked end of the probe is not eliminated, impeding its use as an amplification primer. On the other hand, and since the pfu does not present 5'-3' exonuclease activity, or chain displacement activity, the probe between the amplification primers can not be eliminated and, therefore, functions as a blocker of the amplification process. By contrast, amplification with a DNA polymerase 5'-3' exonuclease enzyme is feasible in this system, since the 5'-3' exonuclease activity eliminates the probe during the elongation process permitting the amplification process.

Consequently, from these results it is guaranteed that generation of a fluorescent signal in amplification systems with pfu DNA polymerase is not in any case due to the presence of remnant 5'-3' exonuclease activities.

Example 5

Detection Assay of Specific Sequences of Nucleic Acids in Fluid Hybridization and an Absence of Polymerization Reaction, Using Probes with Double Fluorescent Labels and pfu DNA Polymerase Activity Since the 3'-5' exonuclease activity of the pfu acts on the unpaired bases at the 3' end of the nucleic acid duplex in the absence of associated polymerization reactions, the possibility of using this property to develop a specific nucleic acid detection system was assayed using double labeled probes (5' TAMRA - - - - FAM 3') and the pfu DNA polymerase activity, in the absence of dNTPs, that could serve as substrate in elongation reactions of nascent chains of nucleic acid.

As an experimental model, the previously described MTB detection system was used. The following substrate DNAs and probes were used:

Substrate DNAs.

Control plasmid (pMTB-Control) obtained by cloning a 335 bp fragment of the IS6110 region of *Mycobacterium tuberculosis* (MTB) in the pBlueScript SK(+) plasmid.

Three mutant sequences (gene amplification products) of 310 bp of the IS6110 region cloned in the previously described control plasmid (pMTB-Control).

Mutant 1P: mutation in the last base of the zone of hybridization with the primers IS and IS-INV. This generates an unlinked base at the 3' end of both primers when it hybridizes with them (See hybridization diagram in FIG. 1B).

Mutant 1F: mutation of the last base of the hybridization zone with primers IS and IS-INV. This generates an unpaired base at the 3' end of both primers when it hybridizes with them (See hybridization diagram in FIG. 1C).

Mutant 2 PF: mutation in the last two bases of the zone of hybridization zone with the primers IS and IS-INV. This generates unpaired nucleotides at the last two bases of the 3' end of both primers when it hybridizes with them (See hybridization diagram in FIG. 1D).

Detection Probe.

The following oligonucleotide was used as a detection probe:

Lion probe IS-INV. Probe with double labeled fluorescence (5' TAMRA - - - - FAM 3') that hybridizes perfectly (100% homology) with the plasmid control sequence (pMTB-Control), and presents unpaired bases at the 3' end with the mutant DNAs 1P, 1F and 2 PF.

The expected action mechanism in this non-nucleic acid polymerization dependent detection system consists in the joining of the probe, by base complementarity with the nucleic acid substrate. If the hybridization is perfect, the 3'-5' exonuclease activity does not function, and no fluorescence is emitted. This would be the case of the assay with the control plasmid pMTB-control. By contrast, if on formation of the plasmid an unpairing occurs at the base at the 3' end of the probe, the 3'-5' exonuclease activity will detect the unpaired base and split the bases emitting fluorescence. This would be the case of the assay with each of the mutants included in the example.

To ensure the functioning of the system the reaction is carried out using the reaction buffers assayed in the previous examples in which the functioning of the pfu 3'-5' exonuclease activity has been demonstrated. Likewise, to facilitate replacement of the catalyzed probes by new probes not modified during the process, similar temperature cycles will be applied to those used in the PCT assays to permit denaturisation and hybridization of the probes with the substrate DNA.

The composition of the reaction mixture was as follows: 0.1 U/μl of pfu DNA polymerase (Biotools), Lion probe IS-INV (0.3 μM) and the specific reaction buffer of pfu. The final volume of the reaction was 20 μl in all cases.

The following temperature cycles were used:
Initial reading five cycles:
First section: 10 s at 58° C., with a curve of 20° C./s
Second section: 10 s at 58° C., with a curve of 20° C./s
Hybridization 30 cycles:
First section: 10 s at 95° C., with a curve of 20° C./s
Second section: 20 s at 58° C., with a curve of 20° C./s
Third section: 60 s at 72° C., with a curve of 20° C./s
Cooling, 1 cycle
First segment: 600 s at 40° C., with a curve of 20° C./s The assay results were monitored in a LightCycler amplification system in real-time.

Figure 6:
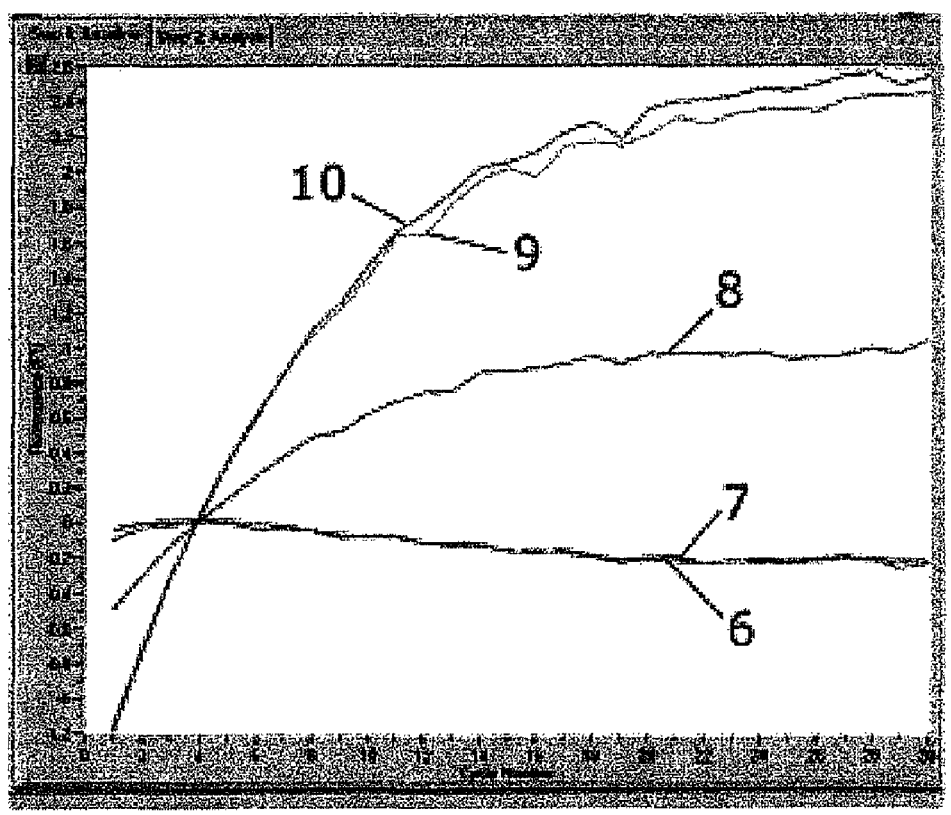
FIG. 6 shows the results of detection by an independent DNA synthesis system shown in example 5, in a graph of fluorescence versus number of cycles.

The results obtained confirm theoretically expected results. FIG. 6 shows how no increase in fluorescent signal was observed in the pMTB-control samples (6) (perfect pairing between probe and substrate) or in the "no-DNA" control sample (7). By contrast, a significant increase in fluorescence was observed in the samples of mutants analyzed, mutant 1F (8), 1P (9), and 2 PF (10). Likewise, different yields of fluorescent signal were observed depending on the type of mutant assayed. Hence, the greatest levels of fluorescence were obtained by assaying mutant sample 1P (9) (unpaired at the penultimate base of the 3' end of the probe) and in mutant 2 PF (10) (unpairing of the last two bases at the 3' end of the probe). By contrast, mutant 1F (8) (unpaired last base of the 3' end of the probe) presented a significant increase, although less than that observed in the last two cases.

The results obtained show the functionality of the system to detect specific sequences of nucleic acids in fluid hybridization systems using the Lion type probes with double fluorescent labeling (5' blocker - - - - 3' fluoride) that presents unpaired bases at the 3' end on hybridizing with the nucleic acid substrate, and the presence of 3'-5' exonuclease proofreading activity, in an independent polymerization mechanism of nucleic acids.

Example 6

Assay to Use the CMV-INV-Block as Probe

The results obtained in examples 1 and 2 show the possibility of detecting specific sequences of nucleic acids using probes with double fluorescent labeling (preferably with the quencher in position 5' and the fluoride in position 3') in gene amplification systems with a DNA polymerase with 3'-5' exonuclease proofreading activity and in those in which the 3' end of the probe presents punctual unpaired bases with the DNA substrate to be identified.

In these conditions, when primer-substrate hybridization occurs, the DNA polymerase recognizes the unpaired bases at the 3' end if the primer, and by the 3'-5' nuclease activity splits the unpaired bases that carry the fluoride. At this point, as the fluoride and the quencher separate fluorescence is emitted.

However, in this system the double labeled fluoride operates simultaneously as an identification probe and also as an amplification primer, since as the unpaired bases are eliminated by the action of the 3'-5' exonuclease, the primer is prepared to prime the elongation of a new chain of DNA. As shown in the results obtained in example 2, using a system of these characteristics provides similar information to that obtained with intercalating fluorides such as SYBR Green. Hence, the non-specific amplification of sequences related to the substrate, or the formation of primer-dimers, can generate a non-specific signal. However, as shown in example 2, generation of a non-specific signal by generating primer-dimer occurs later than that obtained with SYBR Green, by using the signal generation system with 3'-5' nuclease activity using probes that do not operate as primers of the amplification reaction, the detection specificity can be increased.

The present example describes an amplification method in real time that used a double fluorescent labeled probe to generate the signal that has the following structure: A) a sequence of 20 nucleotides that hybridize perfectly (100% homology) with the sequence to be identified; B) a spacer (dS) in position 3' of the oligonucleotide sequence; C) a sequence of 3 nucleotides including two fluorescent markers (quencher and reporter) that do not hybridize with the sequence to be detected.

The following substrate DNAs and oligonucleotides are used:
Substrate DNA.
A plasmid (pCMV) obtained by cloning a conserved fragment of 350 base pairs (bp) of the region encoding the Cytomegalovirus polymerase (CMV) in the pBlueScript SK(+) plasmid.
Amplification Primers and Fluorescent Probes.
Primer CMVF (SEQ ID NO:5). Forward Primer that hybridizes perfectly (100% homology) with the cloned region of the CMV genome in the plasmids pCMV and pMUT-CMV. It functions as an oligonucleotide primer of DNA synthesis.
Primer CMVR (SEQ ID NO:6). Reverse primer that hybridizes perfectly (100% homology) with the cloned region of the CMV genome in plasmids pCMV and pMUT-CMV. It functions as an oligonucleotide primer of DNA synthesis.
CMV-INV-Blok probe (SEQ ID NO:8, 5'-TCCGTCT-GATCGTAGGTGTGAATAA-ds spacer-(TAMRA)tt (FAM-3'). Probe with double fluorescent labeling (5' TAMRA - - - - FAM 3') with the following structure: A) a sequence of 20 nucleotides that hybridizes perfectly (100% homology) with the sequence to be identified; B) a spacer (dS) in position 3' of the oligonucleotide sequence; C) a sequence of 3 oligonucleotides including the two fluorescent labels (quencher and reporter) that does not hybridize with the sequence to be detected. This probe hybridizes with an internal region of the product amplified by the previously described combination of primers CMVF/CMVR.
Amplification reactions were assayed on 1/10 serial dilutions of the plasmid pCMV using a mixture of pfu DNA polymerase and 5'-3' exonuclease DNA polymerase as a source of polymerase activity. The concentration range assayed was of 50,000-50 copies of plasmid/reaction. The composition of the reaction mixture was: 0.1 U/µl of 5'-3' exonuclease DNA polymerase, 0.1 U/ml of pfu DNA polymerase, a mixture of dNTPs, primer CMVR (final concentration: 0.5 µM), primer CMVF (final concentration: 0.5 µM), probe CMV-INV-Block (final concentration: 0.5 µM) and the reaction buffer (Kit Certamp. Biotools), with a final reaction volume of 20 µl in all cases.

As controls, two simultaneous amplification reactions on serial 1/10 dilutions of the plasmid pCMV were used (range: 50,000-50 copies/reaction), using either the DNA polymerase pfu activity, or the DNA polymerase 5'-3' exonuclease activity.

The reaction mixture with pfu DNA polymerase was as follows: Performed with the kit Biotools Pfu DNA polymerase (Biotools), incorporating in the mixture 0.1 u/µl of Pfu DNA polymerase, the reaction buffers, a mixture of dNTPs, primer CMVR (final concentration: 0.5 µM), primer CMVF (final concentration: 0.5 µM), probe CMV-INV-Block (final concentration: 0.5 µM) with a final reaction volume of 20 µl in all cases.

The reaction mixture with DNA polymerase 5'-3' exonuclease was as follows: 0.1 U/ml of DNA polymerase 5'-3' exonuclease (Biotools DNA polymerase), reaction buffer, a mixture of dNTPs, primer CMVR (final concentration: 0.5 µM), primer CMVF (final concentration: 0.5 µM), probe CMV-INV-Block (final concentration: 0.5 µM) and the reaction buffer (Kit Certamp. Biotools), with a final reaction volume of 20 µl in all cases.

The amplification reactions were carried out in a SmartCycler II (Cepheid) amplification system in real-time using the following amplification cycles:

In a first step the temperature was maintained for 360 s at 95.0° C.

In a second step the second cycle was repeated 45 times:
Temperature at 95.0° C. for 5 s.
Temperature at 57.0° C. for 5 s
Temperature at 60.0° C. for 40 s The course of the amplification reaction was monitored in real time by reading in each amplification cycle the fluorescence level in the FAM channel. Like-wise, the amplified products were analyzed in 1.5% ethidium bromide-stained agarose gel.

The results obtained in the assays are shown in Table 2

|  | Plasmid pCMV | |
| --- | --- | --- |
|  | Fluorescence | Gel |
| DNA pol 5'-3' exo | Negative | Positive |
| Pfu DNA Pol | Negative | Negative |
| DNA pol 5'-3' exo + pfu | Positive | Positive |

In all cases, positive results were obtained in agarose gel, the band obtained was 335 bp long, corresponding to the fragment amplified by the pair of primers CMVF/CMVR. In no case were amplification bands the same size as the amplification products of the pair of primers CMV-INV-Blok probe/CMVR observed. These results confirm that the structure of oligonucleotide CMV-INV-Block with an unpaired tail of 3 nucleotides and block of the 3' end by binding of the FAM group correctly blocked the amplification reaction.

The results obtained with DNA polymerase 5'-3' exonuclease (positivity in gel and negative fluorescence, independently of the substrate analyzed) indicated that this activity can remove the bound probe, by 5'-3' exonuclease activity. However, this activity does not affect the integrity of the tail of unpaired nucleotides at position 3' of the probe, so its activity does not generate a fluorescent signal).

The results obtained with pfu DNA polymerase, seem to indicate a blockage of the DNA elongation reaction primed by the CMV-INV-Blok probe subject to the proofreading activity, owing to the presence of the spacer ds. Likewise, the absence of band amplification mediated by the primers CMVF/CMVR, would indicate a blocking of the pfu-mediated amplification reaction, by interposition of the CMV-INV-Blok probe, because of the lack of this chain displacement activity. These results are similar to those obtained in example 4, in which inhibition of the amplification reaction mediated by pfu is also observed, on interposition of a Taq-Man probe.

The results obtained using the combined activities of DNA polymerase 5'-3' exonuclease and pfu DNA polymerase, confirm that the system is operating correctly. Hence, the positivity observed in the agarose gel, confirms the capacity of the DNA polymerase 5'-3' exonuclease activity to degrade the region of the probe that hybridizes with the substrate, permitting the fragment to be amplified. Finally, in association with the amplification reaction, a fluorescent signal was obtained as a result of the 3'-5' nuclease proofreading activity of the pfu DNA polymerase.

The results obtained confirm the use of nucleotides with two distinct regions separated by a spacer, one of which is used to bind to the substrate DNA, which is susceptible to degradation by 5'-3' nuclease activity, and the other is situated in the 3' region of the oligonucleotide, in which the two fluorescent labels are located that can be degraded by 3'-5' nuclease activity, and function as pure detection probes in gene amplification reactions carried out in the presence of a combination of DNA polymerase 5'-3' exonuclease and pfu DNA polymerase activities.

Example 7

Example 7 shows an RNA sequence detection system assay, via an indirect mechanism which links, in a single step, a reverse transcription system (RT), with a subsequent amplification of the cDNA obtained, by an amplification in real time that uses an oligonucleotide with fluorescent double labeling as a primer of the amplification reaction, and a system to generate a fluorescent signal, in the presence of pfu DNA polymerase activity.

To carry out the assay, an amplification system was applied to a conserved zone of the genome of the human immunodeficiency virus (HIV). The following sequences of primer and Lion probe were used:
Substrate RNA. As substrate RNA, two sera of known concentration were used (7.9E+06 and 8.5E+05 copies/ml taken from a panel of sera of HIV of known concentration "HIV-1 RNA Quantification Panel" (Acrometrix). In both cases, RNA was extracted from 200 µl of serum, using the extraction kit "SpeedTools RNA Virus Extraction Kit" (Biotools, Madrid, Spain) and eluting the RNA extracted in a final volume of 20 µl. A total of 5 µl of RNA were used in the reverse transcription/gene amplification reaction.
Reverse primer (antisense): For the primer of the reverse transcription reaction and the subsequent gene amplification reaction an antisense oligonucleotide was used that hybridizes perfectly with the HIV-RNA sequence:
Primer HIV-R1 (SEQ ID NO:9, 5'-GTCCTTTCCAAAT-AGGGTCT-3').
Lion probe: As a forward primer in the cDNA amplification reaction, and as a source of fluorescent signal, a Lion probe was used that hybridizes perfectly with the cDNA made in the reverse transcription process, except at the 3' end base, in which the change in substrate from the 3'-5' nuclease activity of the Pfu DNA polymerase was incorporated:

Lion probe HIV-F1 (SEQ ID NO:10, 5'-GCAGGAA-GATGGCCAGTCAAAGTAATACAA-3'). Forward primer with double labeled ends. The 3' end was labeled with FAM (6-carboxy-fluoresceine) and the 5' end with TAMRA (6-carboxytetramethyl-rhodamine), and FAM blocker. This presents one change in the 3' end base, which should be a Thymine (T) in order to hybridize perfectly with the substrate cDNA.

The reverse transcription/amplification mixture combined in one step, is shown below: 0.1 u/µl of Pfu DNA polymerase (Biotools B&M Labs, Madrid. Spain), MMLV (Sybenzime), reaction buffers, a mixture of dNTPs, Lion probe HIV-F1 (final 0.3 µM) and oligonucleotide HIV-R1 (final 0.5 mM), with a final reaction volume of 50 µl.

With this mixture, the amplification of HIV-RNA previously extracted fro the serum samples (125000 and 25000 copies/reaction, respectively), was assayed, and a no-RNA control.

The amplification reaction was carried out in a Corbett RotorGene 3000 (Corbett) amplification system in real-time using the following amplification cycles:

A.—Reverse Phase Transcription:

In a first step, reverse phase transcription was carried out by incubating at 42° C. for 45 minutes.

B.—Inactivation of Reverse Phase Transcription:

Next, the heat labile enzyme MMLV was inactivated by incubating at 97° C. for 3 minutes.

C.—Amplification Phase of the cDNA Obtained:

In a second step the cycle is repeated 45 times:

Temperature at 95.0° C. for 5 s.

Temperature at 50.0° C. for 3 s.

Temperature at 61.0° C. for 34 s

Temperature at 68.0° C. for 30 s

The course of the amplification reaction was monitored in real-time by reading in each amplification cycle the fluorescence level in the FAm channel, measured in the incubation step at 61° C. Likewise, the amplified products were analyzed in ethidium bromide-stained agarose gel. The results are shown in FIGS. 7A and 7B.

The samples of serum RNA submitted to reverse transcription/amplification in a single step were positive both in the fluorescence curve (see FIG. 7A), with sequential Ct values (smaller value of Ct for the largest initial concentration of RNA), and by agarose gel electrophoresis (see FIG. 7B). By contrast, the phial containing the negative no-RNA control gave a negative result. These results demonstrate the possibility of amplifying RNA and generating a fluorescent signal with Lion RNA probes by an indirect mechanism that uses a cDNA molecule generated in a previous process of reverse transcription as substrate.

The essence of this invention would not be affected by varying the materials, shape, size or arrangement of the components, described in a non-limiting manner, with this description serving to permit an expert in the area to reproduce the object of the invention.

The invention claimed is:

1. A method for detecting a target nucleic acid in a sample, comprising the following steps:
   (1) contacting a sample with a first oligonucleotide primer which hybridizes with said target nucleic acid to leave one or more non-complementary nucleotides unpaired at the 3' end of said first oligonucleotide primer, wherein said first oligonucleotide primer contains a fluorophore quencher at its 5'-end and a fluorophore at its 3'-end, or a fluorophore quencher at its 3'-end and a fluorophore at its 5'-end, and wherein the 3'-nucleotide of said first oligonucleotide primer contains a free hydroxyl group;
   (2) contacting said sample with at least one additional primer, a mixture of nucleotides, and a polymerase enzyme having 3'-5' nuclease activity;
   (3) subjecting the sample containing said first oligonucleotide primer, said mixture of nucleotides, said at least one additional primer, and said enzyme, to real-time PCR; and
   (4) determining whether a measurable signal is produced by said fluorophore during said real-time PCR;
   wherein when said target nucleic acid is present in said sample, said first oligonucleotide primer hybridizes with the target nucleic acid so that nucleic acid extension occurs simultaneously with cleavage of one or more of said non-complementary nucleotides by said enzyme, producing a measurable signal by said fluorophore.

2. The method according to claim 1, wherein the label at the 5' end of said first oligonucleotide primer is a fluorophore quencher and the label at the 3'-end of said first oligonucleotide is a fluorophore.

3. The method according to claim 1, wherein said enzyme, said first oligonucleotide primer, said at least one additional primer, said mixture of nucleotides, and said sample, are present in an aqueous solution.

4. The method according to claim 1, wherein said first oligonucleotide primer is bound to a solid support.

5. The method according to claim 1, wherein said sample is bound to a solid support.

6. The method according to claim 1, wherein said sample is generated by previous gene amplification steps, in vitro transcription (cDNA), or isothermal amplification.

7. The method according to claim 1, wherein said sample is an animal or plant sample, a cell culture, a food product, a water sample, or a soil or air sample.

8. The method according to claim 1, wherein the one or more non-complementary nucleotides unpaired at the 3' end of said first oligonucleotide primer results from a single nucleotide polymorphism in said target nucleic acid sequence.

9. The method according to claim 1, wherein the one or more non-complementary nucleotides unpaired at the 3' end of said first oligonucleotide primer results from a mutation in a codon of said target nucleic acid sequence.

10. A method for detecting a target nucleic acid in a sample, comprising the following steps:
   (1) contacting a sample with an oligonucleotide which hybridizes with said target nucleic acid to leave one or more non-complementary nucleotides unpaired at the 3' end of said oligonucleotide, wherein said oligonucleotide contains a fluorophore quencher at the 5'-end of said oligonucleotide and a fluorophore at the 3'-end of said oligonucleotide, or a fluorophore quencher at the 3'-end of said oligonucleotide and a fluorophore at the 5'-end of said oligonucleotide, and wherein the 3'-nucleotide of said oligonucleotide contains a free hydroxyl group;
   (2) contacting said sample with an enzyme having 3'-5' nuclease activity, a mixture of nucleotides, at least two primers, an enzyme with polymerase activity, and an enzyme with chain displacement activity, 5'-3' nuclease activity, or both; and
   (3) determining whether a measurable signal is produced by said fluorophore;
   wherein when said target nucleic acid is present in said sample, said oligonucleotide hybridizes with the target nucleic acid and functions as a probe to generate a measurable signal without acting as a primer for an extension reaction.

11. The method according to claim 1, wherein the 3'-5' nuclease activity is a proofreading 3'-5' nuclease activity.

12. The method according to claim 11, wherein the polymerase with proofreading 3'-5' nuclease activity is thermostable.

13. A method for detecting a target nucleic acid in a sample, comprising the following steps:
   (1) contacting a sample with an oligonucleotide which hybridizes with said target nucleic acid to leave one or more non-complementary nucleotides unpaired at the 3' end of said oligonucleotide, wherein said oligonucleotide contains a fluorophore quencher at the 5'-end of said oligonucleotide and a fluorophore at the 3'-end of said oligonucleotide, or a fluorophore quencher at the 3'-end of said oligonucleotide and a fluorophore at the 5'-end of said oligonucleotide, wherein the 3'-nucleotide of said oligonucleotide contains a free hydroxyl group, and wherein said oligonucleotide contains modifications in the binding of its bases by non-phosphodiester bonds or by the inclusion of spacers, to protect these positions from 3'-5' nuclease activity;
   (2) contacting said sample with an enzyme having 3'-5' nuclease activity; and
   (3) determining whether a measurable signal is produced by said fluorophore;
   wherein when said target nucleic acid is present in said sample, said one or more non-complementary nucleotides unpaired at the 3' end of said oligonucleotide are cleaved by said enzyme, producing a measurable signal by said fluorophore.

14. The method according to claim 13, wherein the oligonucleotide is modified at its 3' end to protect the hydrolysis of certain positions.

15. The method according to claim 10, wherein the oligonucleotide is modified to inhibit the 5'-3' nuclease activity of the polymerase with chain displacement activity.

16. A method for detecting a target nucleic acid in a sample, comprising the following steps:
   (1) contacting a sample with an oligonucleotide which hybridizes with said target nucleic acid to leave one or more non-complementary nucleotides unpaired at the 3' end of said oligonucleotide, wherein said oligonucleotide contains a fluorophore quencher at the 5'-end of said oligonucleotide and a fluorophore at the 3'-end of said oligonucleotide, or a fluorophore quencher at the 3'-end of said oligonucleotide and a fluorophore at the 5'-end of said oligonucleotide, and wherein the 3'-nucleotide of said oligonucleotide contains a free hydroxyl group;
   (2) contacting said sample with an enzyme having 3'-5' nuclease activity; and
   (3) determining whether a measurable signal is produced by said fluorophore;
   wherein said method is performed in a hybridization system in the absence of a polymerization reaction, and wherein when said target nucleic acid is present in said sample, said one or more non-complementary nucleotides unpaired at the 3' end of said oligonucleotide are cleaved by said enzyme, producing a measurable signal by said fluorophore.

17. The method according to claim 16, wherein production of the measurable signal is monitored in real-time.

18. A kit for determining a nucleic acid sequence in a sample, wherein said kit comprises an oligonucleotide that contains a sequence complementary to the nucleic acid sequence to be determined, but with one or more non-complementary bases at the 3' end of the oligonucleotide, wherein said oligonucleotide contains a fluorophore quencher at the 5'-end of said oligonucleotide and a fluorophore at the 3'-end of said oligonucleotide, or a fluorophore quencher at the 3'-end of said oligonucleotide and a fluorophore at the 5'-end of said oligonucleotide, wherein the 3'-nucleotide of said oligonucleotide contains a free hydroxyl group, and wherein said oligonucleotide is modified at its 3' end to protect the hydrolysis of certain positions, and wherein said kit further comprises a polymerase enzyme having 3'-5' nuclease proofreading activity.

19. The kit according to claim 18, further comprising at least one additional oligonucleotide primer complementary to the nucleic acid to be determined.

20. The kit according to claim 18 wherein the 3' end of said oligonucleotide is labelled with a fluorophore and the 5' end of said oligonucleotide is labelled with a fluorophore quencher.

21. The kit according to claim 18, further comprising deoxynucleotides.

22. The method according to claim 1, wherein the label at the 5' end of said first oligonucleotide primer is a fluorophore and the label at the 3'-end of said first oligonucleotide primer is a fluorophore quencher.

23. The kit according to claim 18 wherein the 3' end of said oligonucleotide is labelled with a fluorophore quencher and the 5' end of said oligonucleotide is labelled with a fluorophore.

* * * * *

SEQUENCE LISTING

<160> NUMBER OF SEQ ID NOS: 11

<210> SEQ ID NO 1
<211> LENGTH: 29
<212> TYPE: DNA
<213> ORGANISM: Artificial Sequence
<220> FEATURE:
<223> OTHER INFORMATION: Synthetic oligonucleotide primer

<400> SEQUENCE: 1
cgcaaagtgt ggctaaccct gaaccgtga                              29

<210> SEQ ID NO 2
<211> LENGTH: 30
<212> TYPE: DNA
<213> ORGANISM: Artificial Sequence
<220> FEATURE:
<223> OTHER INFORMATION: Synthetic oligonucleotide primer

<400> SEQUENCE: 2
catcgtggaa gcgacccgcc agcccaggat                             30

<210> SEQ ID NO 3
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 3
cgccaactac ggtgtttacg g                                      21

<210> SEQ ID NO 4
<211> LENGTH: 23
<212> TYPE: DNA
<213> ORGANISM: Artificial Sequence
<220> FEATURE:
<223> OTHER INFORMATION: Synthetic oligonucleotide primer

<400> SEQUENCE: 4
cgacacatag gtgaggtctg cta                                    23

<210> SEQ ID NO 5
<211> LENGTH: 19
<212> TYPE: DNA
<213> ORGANISM: Artificial Sequence
<220> FEATURE:
<223> OTHER INFORMATION: Synthetic oligonucleotide primer

<400> SEQUENCE: 5
gatagacaca cactgcaaa                                         19

<210> SEQ ID NO 6
<211> LENGTH: 16
<212> TYPE: DNA
<213> ORGANISM: Artificial Sequence
<220> FEATURE:
<223> OTHER INFORMATION: Synthetic oligonucleotide primer

<400> SEQUENCE: 6
ggtgggacct attcgt                                            16

<210> SEQ ID NO 7
<211> LENGTH: 22
<212> TYPE: DNA

```
<213> ORGANISM: Artificial Sequence
<220> FEATURE:
<223> OTHER INFORMATION: Synthetic oligonucleotide primer

<400> SEQUENCE: 7
ttcacaccta cgatcagacg ga                                              22

<210> SEQ ID NO 8
<211> LENGTH: 25
<212> TYPE: DNA
<213> ORGANISM: Artificial Sequence
<220> FEATURE:
<223> OTHER INFORMATION: Synthetic oligonucleotide primer

<400> SEQUENCE: 8
tccgtctgat cgtaggtgtg aataa                                           25

<210> SEQ ID NO 9
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 9
gtcctttcca aatagggtct                                                 20

<210> SEQ ID NO 10
<211> LENGTH: 30
<212> TYPE: DNA
<213> ORGANISM: Artificial Sequence
<220> FEATURE:
<223> OTHER INFORMATION: Synthetic oligonucleotide primer

<400> SEQUENCE: 10
gcaggaagat ggccagtcaa agtaatacaa                                      30

<210> SEQ ID NO 11
<211> LENGTH: 34
<212> TYPE: DNA
<213> ORGANISM: Mycobacterium tuberculosis

<400> SEQUENCE: 11
gcgtttcaca ccgattggga cttggcactc ccgt                                 34
```